(12) United States Patent
Robinette

(10) Patent No.: US 6,966,087 B2
(45) Date of Patent: Nov. 22, 2005

(54) PEDIATRIC IMMOBILIZER

(76) Inventor: Lydia Marie Robinette, 6201 Apache Way, Grove City, OH (US) 43123

( * ) Notice: Subject to any disclaimer, the term of this patent is extended or adjusted under 35 U.S.C. 154(b) by 0 days.

(21) Appl. No.: 10/489,294

(22) PCT Filed: Sep. 11, 2002

(86) PCT No.: PCT/US02/28810
§ 371 (c)(1),
(2), (4) Date: Jul. 12, 2004

(87) PCT Pub. No.: WO03/022185
PCT Pub. Date: Mar. 20, 2003

(65) Prior Publication Data
US 2004/0244114 A1 Dec. 9, 2004

Related U.S. Application Data
(60) Provisional application No. 60/322,292, filed on Sep. 12, 2001.

(51) Int. Cl.⁷ ............................................. A61G 1/00
(52) U.S. Cl. ................. 5/625; 5/626; 5/628; 5/655; 5/637
(58) Field of Search ................. 5/625–628, 655, 5/637; 128/870, 875

(56) References Cited

U.S. PATENT DOCUMENTS

| 4,601,075 | A | * | 7/1986 | Smith | 5/628 |
| 4,979,520 | A | * | 12/1990 | Boone et al. | 128/870 |
| 5,014,724 | A | * | 5/1991 | Miller | 128/870 |
| 5,425,381 | A | * | 6/1995 | Peterson et al. | 5/652 |
| 5,515,869 | A | * | 5/1996 | Powell et al. | 5/628 |
| 5,634,222 | A | * | 6/1997 | Zwickey | 5/628 |
| 5,860,176 | A | * | 1/1999 | Norberg | 5/628 |
| 6,170,486 | B1 | * | 1/2001 | Islava | 128/869 |
| 6,244,270 | B1 | * | 6/2001 | Lutian et al. | 128/869 |

* cited by examiner

Primary Examiner—Michael Trettel
(74) Attorney, Agent, or Firm—Dinsmore & Shohl LLP

(57) ABSTRACT

A pediatric spinal immobilization device and method for immobilizing a pediatric trauma patient are provided. The immobilization device in one embodiment is releasably secured to an adult-sized backboard, and in another embodiment is provided with a removably contained infant-sized backboard. The immobilization device provides body-straps mounted along a central section of the device, and individual appendage-restraints to permit removal of the body-straps without compromising control over the appendages of the injured patient. Compressible, crescent-shaped headblocks are tightly yet removably fastened to the immobilization device. A harness of the immobilization device helps secures the injured patient over an included adjustable elevation device and when used in conjunction with the headblocks, significantly reduces the risk of further injury from lateral and flexion movement of the head.

20 Claims, 7 Drawing Sheets

PEDIATRIC IMMOBILIZER

The present invention relates to a splinting device for spinal immobilization and airway control of a pediatric trauma patient, and specifically to an improved pediatric immobilizer having centrally mounted body-straps, individual appendage-restraints, compressible crescent-shaped headblocks, and a three-point harness to help secure a pediatric trauma patient over an included adjustable device providing variable levels of thoracic elevation and airway positioning.

Pediatric patients have a propensity for spinal cord injuries relating to a proportionately large head-to-body mass ratio. This creates relative cervical flexion when placed on a standard backboard for immobilization. It is of paramount importance to keep the pediatric patient in neutral cervical alignment as well as immobilized during handling and transportation to an appropriate medical facility.

The most common method of aligning a child's cervical spine is by stuffing towels or foam pads under the child for thoracic elevation. There is no efficient and standard means of determining the amount of thoracic padding required for a pediatric patient under the age of eight years, but medical studies have determined that somewhere in the range of 0.5 cm to 4.1 cm of elevation would be required. This wide elevation range leaves the provider prefiguring and amending the pediatric immobilizer in order to place a correct number of towels or pads under the pediatric patient. This is inefficient and further increases the potential for further cervical injury due to unnecessary cervical disturbance and/or incorrect positioning.

Currently, there is not an efficient and/or standardize means of providing safety through infant restraint during transport. Additionally, soft collars used to prevent undesired head movement, do not effectively immobilize the cervical spine of the pediatric patient. Cervical collars of semi-rigid material are difficult to fit young pediatric patients. Without a perfect fit, such devices allow hyperextension and/or flexion of the neck of the pediatric patient.

Thus, there is a need for an efficient and standardized means of consistently providing proper spinal alignment and immobilization to a pediatric patient that does not subject the pediatric patient to an increased risk of neurological injury. Additionally, there is a need for a device that also prevents undesired head movement, immobilization, and cervical alignment for the infant patient which is too small for the use of a cervical collar, during transport.

The present invention is a pediatric immobilizer which can accommodate pediatric patients of different sizes. The pediatric immobilizer in a first embodiment (hereinafter referred to as the "pediatric version") provides a fabric cover for transporting a pediatric patient, from the age of about two months to eight years, suffering from a trauma to the head, neck, or back. The cover slips over a conventional backboard, such as the type used for rigid support to transport adult patients suffering from a head, neck, and/or back injuries. For infants under the age of about three months or about fifteen pounds, the pediatric immobilizer in a second embodiment (hereinafter referred to as the "infant or neonatal version") maintains the same features as the pediatric version but is sized to accommodate such infant patients. For such an arrangement, provided is a suitable infant backboard.

In the pediatric version, the cover of the pediatric immobilizer is removably affixed to a conventional backboard using adjustable fasteners, which form fit the cover to the backboard. Because the cover is shorter than the length of the backboard, handles at the lower end of the backboard are exposed to permit gripping by paramedics. At the upper end of the backboard, paramedics may grip the corner handles through corner cutouts provided in the cover.

In the infant version, the infant backboard is inserted within the cover via an envelope opening. In one embodiment, the infant backboard is foam padded. In another embodiment, the infant backboard is provided with a pair of holes in each long side. Additional holes that correspond to those provided in the infant backboard are included in the cover. Together, these holes are used to accommodate preferably ball-loc pins that permit mounting of the infant backboard to an isolette. For this embodiment, spring load latches or slots are provided on the sides of the isolette to engage the ball-loc pins thereby securely mounting the infant immobilizer thereon. In still another embodiment, the cover and/or interior board of the infant immobilizer and the isolette mattress may include hook and loop fastening material to provide a secure mounting of the immobilizer.

Accordingly, it should be appreciated to those persons skilled in the related art that other configurations and arrangements of mechanical fasteners may be provided in order to mount securely the infant immobilizer to the isolette. The advantage of such an arrangement is that an infant patient need not be removed from the pediatric immobilizer in order to be placed in the isolette, thereby minimizing the risk of further injury to the infant patient.

It is to be appreciated that the infant immobilizer along with providing infant cervical immobilization can also be used as a safety restraint in conjunction with isolette transports. As such, the device is and effective an standardized means for providing safety through infant restraint during transport by using a multi-point securing system to protect and restrain the neonate in the event of untoward motion during transport. The head blocks serve to maintain endotracheal positioning by controlling lateral head movement which may otherwise displace the tube either into the main-stem bronchus or up into the pharynx compromising airway maintenance.

The thoracic pneumatic elevating devise may be used to position the infant with head extension to move the tongue and epiglottis away from the posterior pharyngeal wall during endotracheal insertion. After tube insertion, the thoracic elevating devise prevents flexion of the head and neck thus protecting the airway from occlusion. The thoracic elevating devise may also reduce the risk of obstructive apnea in the non-intubated patient.

In both versions of the pediatric immobilizer, headblocks are removably affixed to the cover, such as with hook-and-loop type fasteners, in order to adjust their position such that they are snug to the patient's head. The blocks are oppositely crescent shaped to curve around the side of the patient's head, and engage the neck between the head and shoulders. The headblocks permit a degree of wrap to the parietal and mandibular regions to increase the surface area interface between the head and headblocks. As such, the pediatric immobilizer is form fitting and in conjunction with the harness feature it uses counter-force to prevent undesired head, neck, and shoulder movement, and thereby significantly reduces the risk of lateral rotation of the head.

The headblocks are soft and may be compressed so that a paramedic can inspect the pediatric patient's ear without removing the block away from the patient's head. The foam insert of each headblock may be removed via an envelope opening in the headblock's cover material. Straps are provided to surround the face of the patient and prevent movement thereof.

In both versions of the pediatric immobilizer, body straps are provided at three positions along the longitudinal axis of the patient's body to complete a nipple-waist-knee restraining procedure. The body straps are centrally mounted to the cover to permit a tighter fit on the patient. Individual arm-restraints are provided on the pediatric version which permit the removal of the chest or abdominal straps during examination or other procedures, without risking loss of control over the patient's arms or comprising peripheral IV access.

A set of individual leg straps is provided which allows for sizing and prevents leg movement in the case of Intra-Osseous insertion or infusion. All the above-mentioned straps use fasteners, such as for example, hook-and-loop type fasteners, in order to be secured around the patient's body. Finally, a three-point shoulder harness is provided which secures between the patient's legs to discourage caudal movement of the body. Additionally, the harness properly maintains the patient's back in the thorax region over an inflatable bladder provided on the cover.

In both versions of the pediatric immobilizer, for enabling cervical neutral alignment via thoracic elevation and opening an airway, an inflatable bladder is releasably secured to or removably contained in a pocket on the front cover. The bladder when inflated allows a caregiver to raise or lower the thorax in small increments to align the external auditory means with the shoulders as the guideline to providing neutral cervical alignment and optimal airway opening. It is to be appreciated that the system of headblocks, head straps, chin straps, chest straps, abdominal straps, arm straps, leg straps, shoulder harness and the inflatable bladder function to immobilize and correctly align the cervical spine of a pediatric patient.

When not in use, the cover of the pediatric version may be rolled into a compact form, and maintained as such by a protective wrap, which encircles the rolled cover and affixes to itself. Additionally, in both versions the inflatable bladder may be removed from the pocket, allowing for its repair in the event of mechanical failure, or for machine-washing of the cover.

In one aspect of the invention, a spinal immobilization device for a pediatric patient suffering from a trauma to the head, neck or back is provided. The immobilization device comprises a cover having on a front portion a first securing element, a plurality of releasably attachable body straps each having a midsection mounted along a central section of the front portion to provide a degree of wrap around the pediatric patient, and at least a pair of releasably attachable arm and leg restraints. An elevation device on the front portion is also provided. The device further comprises a pair of compressible crescent-shaped headblocks each having, substantially covering on a side, a second securing element. With the second securing elements, the headblocks can be tightly yet removably secured to the first securing element in a location that significantly minimizes the risk of further injury due to undesirable lateral and flexion head movement of the pediatric patient when secured to the device. A harness is also provided wherein a first end is mounted along the central section of the front portion such that the harness passes between the legs of the pediatric patient when accommodated in the device. Second and third ends of the harness are mounted to the front portion such that the harness provides a degree of wrap to the headblocks and helps maintain the pediatric patient on the elevation device when accommodated in the device.

In another aspect of the invention, a method of supporting a pediatric patient on an adult sized backboard, having a plurality of hand slots, is provided. The method comprises securing a pliable cover having a front portion and a rear portion to the backboard with releasably adjustable attachments of the cover looping through a pair of the hand slots of the backboard. Additionally, at least one pair of releasable side flaps are provided to provide a degree of wrap of the cover to the backboard. The pediatric patient is secured to the cover using a plurality of centrally mounted body straps providing a degree of wrap around a least the chest, waist, and knees of the pediatric patient, and a plurality of individual appendage restraints such that the body straps may be removed without losing control over the pediatric patient's appendages. A pair of compressible, crescent-shaped headblocks work in conjunction with the harness, forehead, and chin strap to significantly reduce the risk of further injury due to undesirable flexion and lateral movement of the patient's head. Each of the pair of headblocks has on a rear side a second mating surface such that it is tightly yet removably attached to the first mating attachment. The method further comprises inflating an inflatable bladder provided to the cover to provide varying degrees of elevation to obtain neutral cervical alignment and/or optimal airway opening by elevating the pediatric patient's back in the thorax region, and adjusting a three-point harness provided on the cover to help retain the pediatric patient on the inflatable bladder and to provide a degree of wrap to the headblocks.

Other features and advantages of the present invention will be apparent in light of the description of the invention embodied herein.

The following detailed description of the embodiments of the present invention can be best understood when read in conjunction with the accompanying drawings, where like structure is indicated with like reference numerals, and in which.

Figure 1:
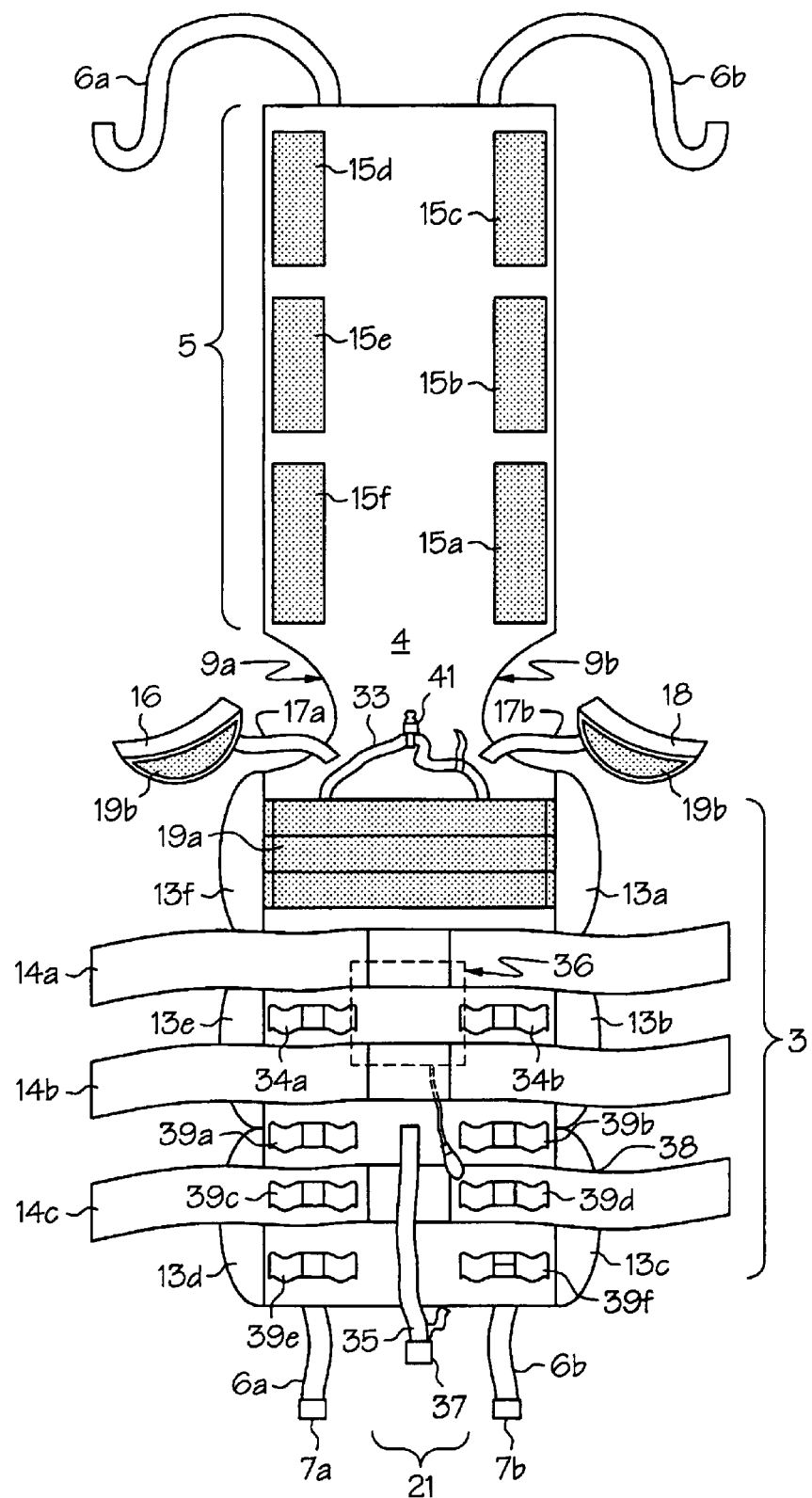
FIG. 1 is a front perspective view of a pediatric spinal immobilization device according to the present invention.

A method and apparatus for immobilizing a pediatric patient suffering from a trauma to the head, neck, and/or back are described. For a first embodiment of the invention, reference is made to FIGS. 1, 2a, and 2b. A front perspective view of a pediatric spinal immobilization device 2 is illustrated by FIG. 1. The device 2 of this embodiment provides a surface in the form of a fabric cover 4 on which to immobilize a pediatric patient, preferably from the age of about two months to eight years, suffering from a trauma to the head, neck and/or back. The cover 4 has a front portion 3 and a rear portion 5 which fit over and under, in a clamshell fashion, a flat, rigid panel 10, such as illustrated in FIGS. 2a and 2b.

Figure 2A:
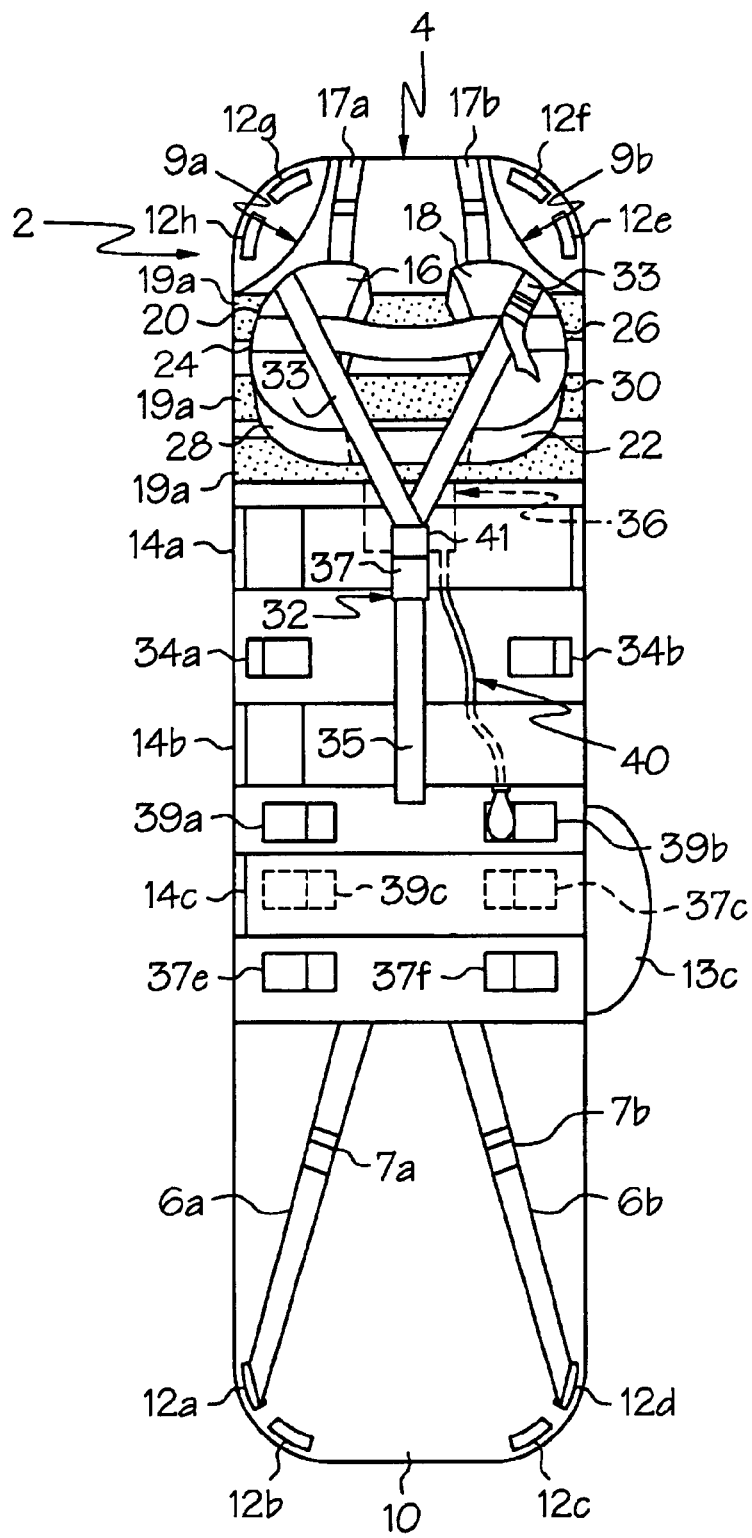
FIGS. 2a and 2b are front and back perspective views, respectively, of the embodiment of FIG. 1 attached to an adult-sized backboard.
Figure 2B:
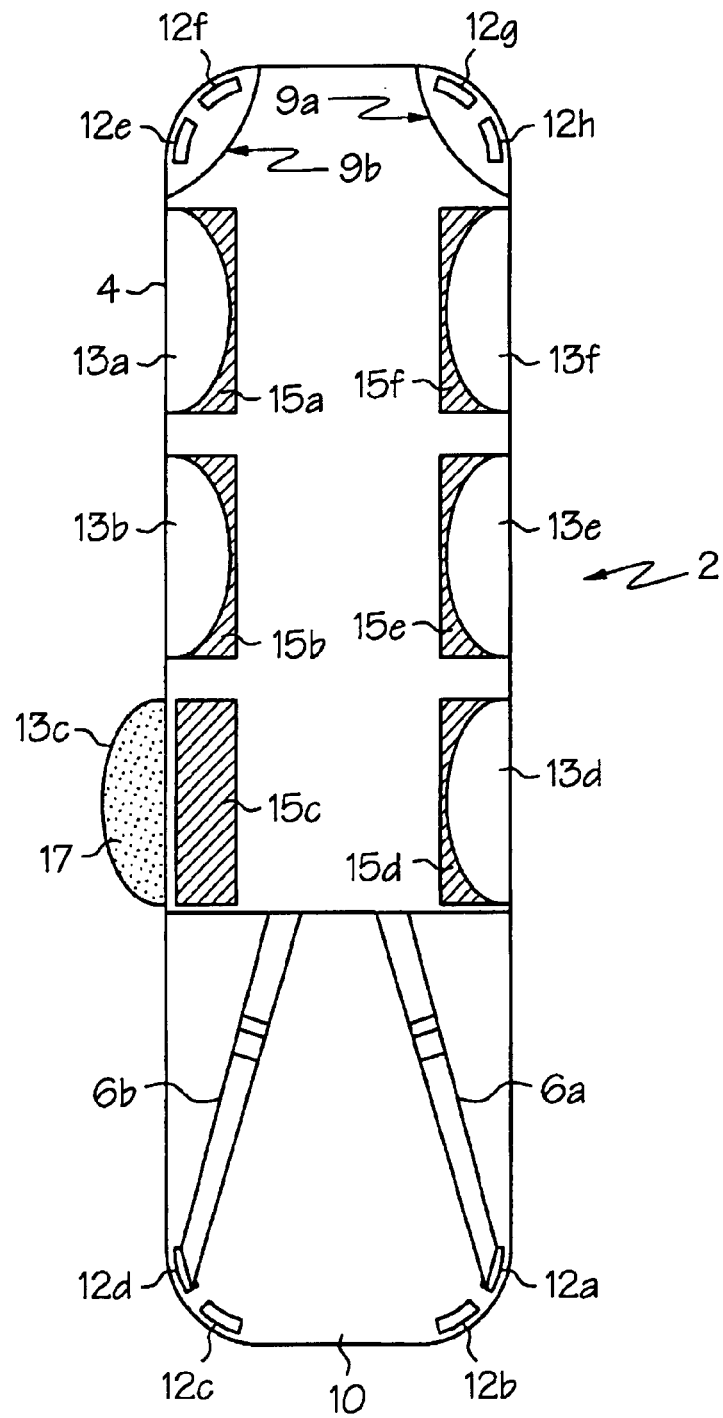

As shown in FIGS. 2a and 2b, the panel 10 preferably used with this embodiment is provided with a plurality of slots 12a, 12b, 12c, 12d, 12e, 12f, 12g, and 12h, adjacent its perimeter edge which serves as hand receptacles for the hands of the rescuers. For other embodiments, the panel 10 may be provided with other types of hand receptacles or gripping surfaces.

A pair of the slots at an end portion of the panel 10, such as 12a and 12d, serves to create adjustable anchoring points for straps 6a and 6b provided at both ends of the cover 4 such that cover 4 may be secured to the flat, rigid panel 10. As illustrated, each strap 6a and 6b loops through an associated anchoring point, slots 12a and 12d, and reattaches to itself by a hook and latch or other appropriate fastening system 7a and 7b, respectively. Because the cover 4 fits over the panel 10 in a clamshell fashion, cutouts 9a and 9b are provided in the cover 4. The cutouts 9a and 9b expose the slots 12e, 12f, 12g, and 12h at the corners of the panel 10 at the opposite end portion of the panel 10 when the cover 4 is fitted over the panel 10, as shown by FIGS. 2a and 2b. Accordingly, the ability of rescuers to use a majority of the slots located in the end portions of the panel 10 for control is unaffected by the cover 4 when fastened thereon.

The panel 10 in the embodiment illustrated by FIGS. 2a and 2b, is preferably a conventional, adult-sized backboard which serves as the major supporting device for the patient's body. The panel 10 may be constructed from several suitable, non-porous materials such as coated wood, plastic, fiberglass, composites, or cellular type materials. The primary factors for material selection are ease of manufacture, strength of material, expense, and washing ability. Additionally, the panel 10 may be radio-transparent.

Typically, the width of the panel 10 differs from one manufacturer to another, and can range from about 16 to about 19 inches. Therefore, in order to provide a degree of wrap of the cover 4 over a panel 10 of varying widths, the front portion 3 of the cover 4 is provided with a plurality of side flaps 13a, 13b, 13c, 13d, 13e, and 13f. Releasable fastening elements 15a, 15b, 15c, 15d, 15e, and 15f are located on the cover 4, and on each side flap such that the flaps 13a, 13b, 13c, 13d, 13e, and 13f may be properly secured to the cover. For illustration purposes, the releasable fastening elements are shown on the rear portion 5 of the cover 4, but may also be conveniently provided on the front portion 3 of the cover 4. Preferably, the releasable fastening elements 15a, 15b, 15c, 15d, 15e, and 15f are loop patches, such that a corresponding hook patch 17 (shown only on side flap 13c is provided on a side of each side flap 13a, 13b, 13c, 13d, 13e, and 13f in order to secure the flaps to the cover 4 over a range of positions that provide a snug fit of the cover 4 to the panel 10. Those persons skilled in the art will recognize that other types of fastening elements may be used, such as adjustable straps with quick release buckles, zippers, and the like, in order to provide a snug and secure fit of the cover 4 to the panel 10.

To secure the pediatric patient to the front portion 3 of the cover 4, a plurality of flexible body straps 14a, 14b, and 14c are provided to the cover 4, as illustrated by FIG. 1. A midsection of each body strap 14a, 14b, and 14c is secured along a central section 21 of the cover 4 in order to provide a degree of wrap of the body straps around the pediatric patient. Preferably, the body straps 14a, 14b, and 14c are provided at three positions along the longitudinal axis of the patient's body to complete a nipple-waist-knee restraining procedure. In particular, strap 14a secures the shoulder and chest area of the patient, strap 14b secures the abdominal/pelvic region of the patient, and strap 14c secures the patient's legs. It is to be appreciated that the body straps 14a, 14b, and 14c as positioned, discourage caudal movement of the pediatric patient and provide for the safe transport to an appropriate medical facility. Hook-and-loop fastening materials or other appropriate fastening elements are located at the free ends of each strap 14a, 14b, and 14c, such that each body strap 14a, 14b, and 14c may properly reattach to itself in order to tightly yet releasably secure the body of the pediatric patient.

Headblocks 16 and 18 are movably affixed to the front portion of the cover 4, proximate the cutouts 9a and 9b, by adjustable straps 17a and 17b, respectively. The headblocks 16 and 18 may be positioned over a wide range of locations on a first securing element 19a. A corresponding second securing element 19b is provided to a significant extent on a side of each of the headblocks 16 and 18, such that when the first and second securing elements come into contact, the headblocks are firmly but releasably secured to the front portion 3 of the cover 4. Preferably, the securing elements 19a and 19b are hook-and-loop fastening materials, with the first securing element 19a provided to substantially cover the area between the cutouts 9 and the chest-body strap 14a from edge to edge. With this area covered by the first securing element 19a, the headblocks 16 and 18 may be fitted efficiently and easily by emergency personnel around patients with various head sizes.

In addition to the convenience of a wide range of locating positions for the headblocks 16 and 18, the patient's head is also properly restrained by the crescent-shape design of the headblocks 16 and 18. Each of the headblocks 16 and 18 are formed of a fabric cover having a compressible foam insert which may be compressed so that a paramedic can inspect the pediatric patient's ear without removing the block away from the patient's head. The foam inserts of headblocks 16 and 18 may be removed from a perpendicular envelope opening (not shown) provided in the respective fabric cover.

In addition, the headblocks 16 and 18 are crescent shaped to curve around the sides of the patient's head and engage the neck between the head and shoulders. In this manner, the blocks 16 and 18 permit a degree of wrap to the parietal and mandibular regions to increase the surface area interface between the head and headblocks thereby providing a stable immobilizing arrangement which significantly prevents undesirable lateral movement of the head. The headblocks 16 and 18, when placed firmly against the patient's head and shoulders and used in conjunction with the forehead and chin straps, significantly reduce the risk of further injury from lateral and flexion movement of the head.

Head and chin straps 20 and 22, respectively, are further provided to stabilize and minimize the movement of the patient's head. In particular, the head strap 20 folds over headblock 16, the patient's forehead area, and headblock 18 to properly restrain the patient's upper head area. The ends of the head strap 20 are releasably fastened to the headblocks 16 and 18 at points 24 and 26, respectively, preferably via hook-and loop fastening materials or other appropriate fastening elements. Chin strap 22 folds over headblock 16, the patient's chin area, and headblock 18 to properly restrain the patient's lower head area and chin. The ends of the chin strap 22 are fastened to the headblocks 16 and 18 at points 28 and 30, respectively, preferably via hook-and-loop fastening materials or other appropriate fastening elements.

A three-point harness 32 is provided to snugly fit over the patient, and to provide a degree of wrap to the pair of headblocks 16 and 18. The harness 32 has a first adjustable strap 33 and a second strap 35. The first adjustable strap 33 is attached at its ends to the cover 4, adjacent the first attachment surface 19a of the cover 4, and is configured to extend over each headblock 16 and 18 and the shoulders of the patient. The second strap 35 is attached within the central section 21 of the cover 4, between the abdomen and leg body straps 14b and 14c, respectively, such that it extends from underneath and between the legs of the pediatric patent. Preferably, a quick release fitting 37 or other fastening element is provided to adjust the length of strap 35 and to releasably engage a sliding buckle 41 or other fastening element. The sliding buckle 41 when attached to the fitting 37 pulls the first strap 33 down over the headblocks 16 and 18 and the shoulders of the patient, in a v-shape, and provide a degree of wrap of the harness to headblocks 16 and 18, which is best shown by FIG. 2a.

To minimize the risk of losing control over the limbs or compromising peripheral intravenous access of a pediatric patient during examination or other procedures, individual appendage restraints are provided to the cover 4. In particular, arm restraints 34a and 34b are provided to permit the removal of the chest and/or abdomen body straps 14a and 14b, respectively. Additionally, a set of leg restraints 39a, 39b, 39c, 39d, 39e and 39f are provided to substantially restrain leg movement of the patient, and to accommodate patients of various lengths. Hook-and-loop fastening material or other appropriate fastening elements are located on the free ends of each restraint such that each respective restraint may properly reattach to itself in order to tightly yet releasably secure a respective appendage of the pediatric patient. It is to be appreciated that the restraint system of the pediatric spinal immobilization device 2 which includes body straps 14a, 14b, and 14c, harness 32, and arm and leg restraints 34 and 39, respectively, serves to discourage caudal movement of the pediatric patient's body in order to minimize the risk of further injury.

Figure 3A:
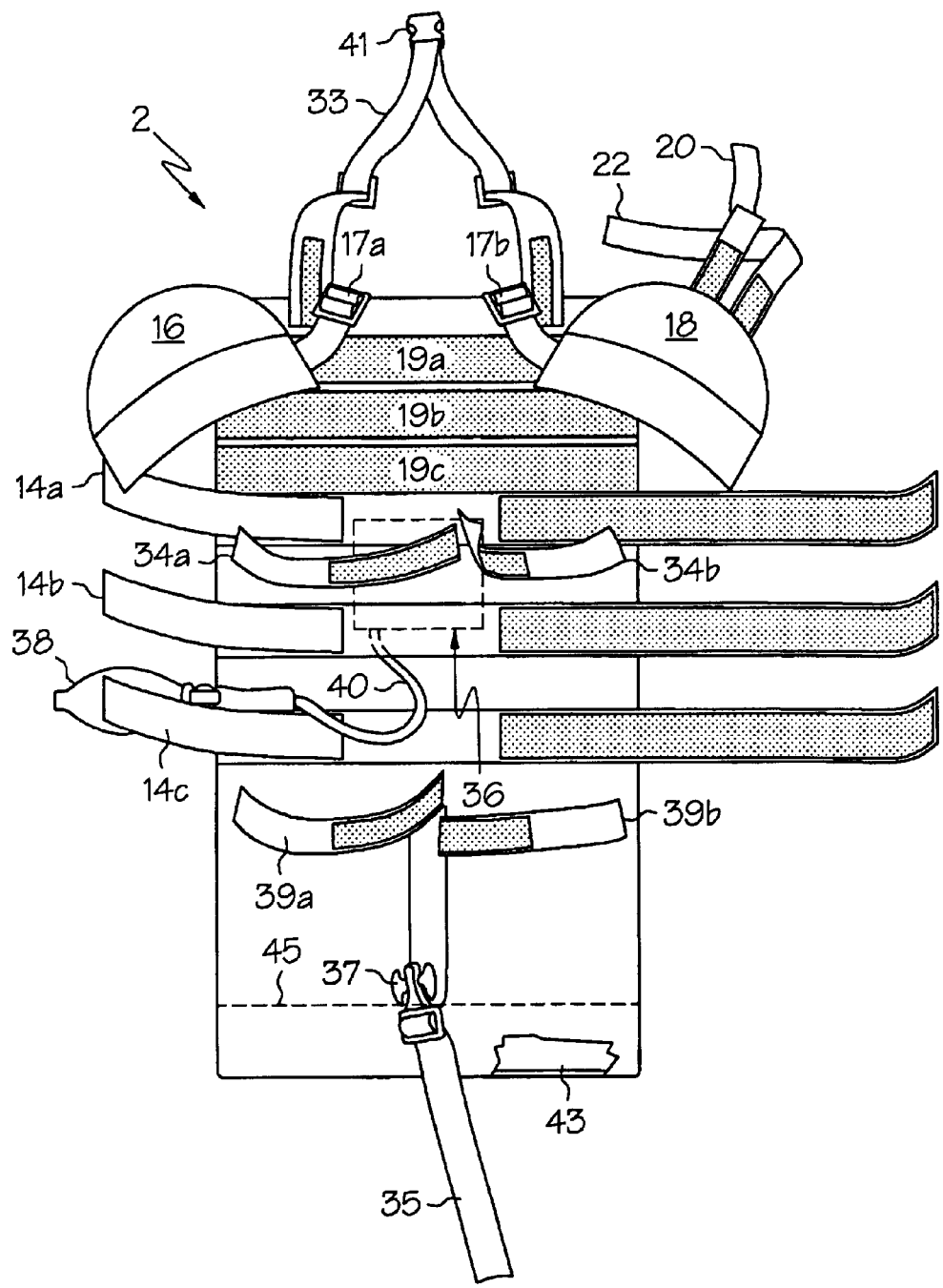
FIGS. 3a and 3b are perspective views of other embodiments of a pediatric spinal immobilization device according to the present invention.

A front perspective view of another embodiment of the pediatric spinal immobilization device 2 of the present invention is shown in FIG. 3a. In this embodiment, the same features that were mentioned with respects to the embodiment of FIG. 1 are labeled with like numbers, and for convenience, only the differences between in this embodiment and the FIG. 1 embodiment will be discussed.

In the embodiment illustrated in FIG. 3a, the spinal immobilization device 2 is sized such that an infant or neonatal patient under the age of about two months or about fifteen pounds may be secured in a cervical neutral position double in situations of potential neurological compromise subsequent to trauma. It is also to be appreciated that the neonatal embodiment also may function as a securing and restraining system to encourage safe transport by caregivers using a cart or an isolette.

For this embodiment, a flat, rigid infant backboard 43 is sized to fit completely within the fabric cover 4, via an envelope opening, indicated by dashed-line 45, provided in the cover 4. The infant backboard 43 may be padded, such as by the use of a polymeric foam. Preferably, the dimension of the cover 4 is from about 29.5 cm in width, about 60 cm in length, and about 1.75 cm in height. It is to be appreciated that the dimensions of the infant backboard 43 are slightly less than the cover 4 in order to be contained therein. The infant backboard 43 is secured within the cover 4 in a conventional manner, such as hook-and-loop, snaps, zippers, buttons, and the like. Preferably, the infant backboard 43 is radio-transparent. The infant backboard 43 may be removed from cover 4, such that both can be cleaned or/and replace when necessary.

Figure 3B:
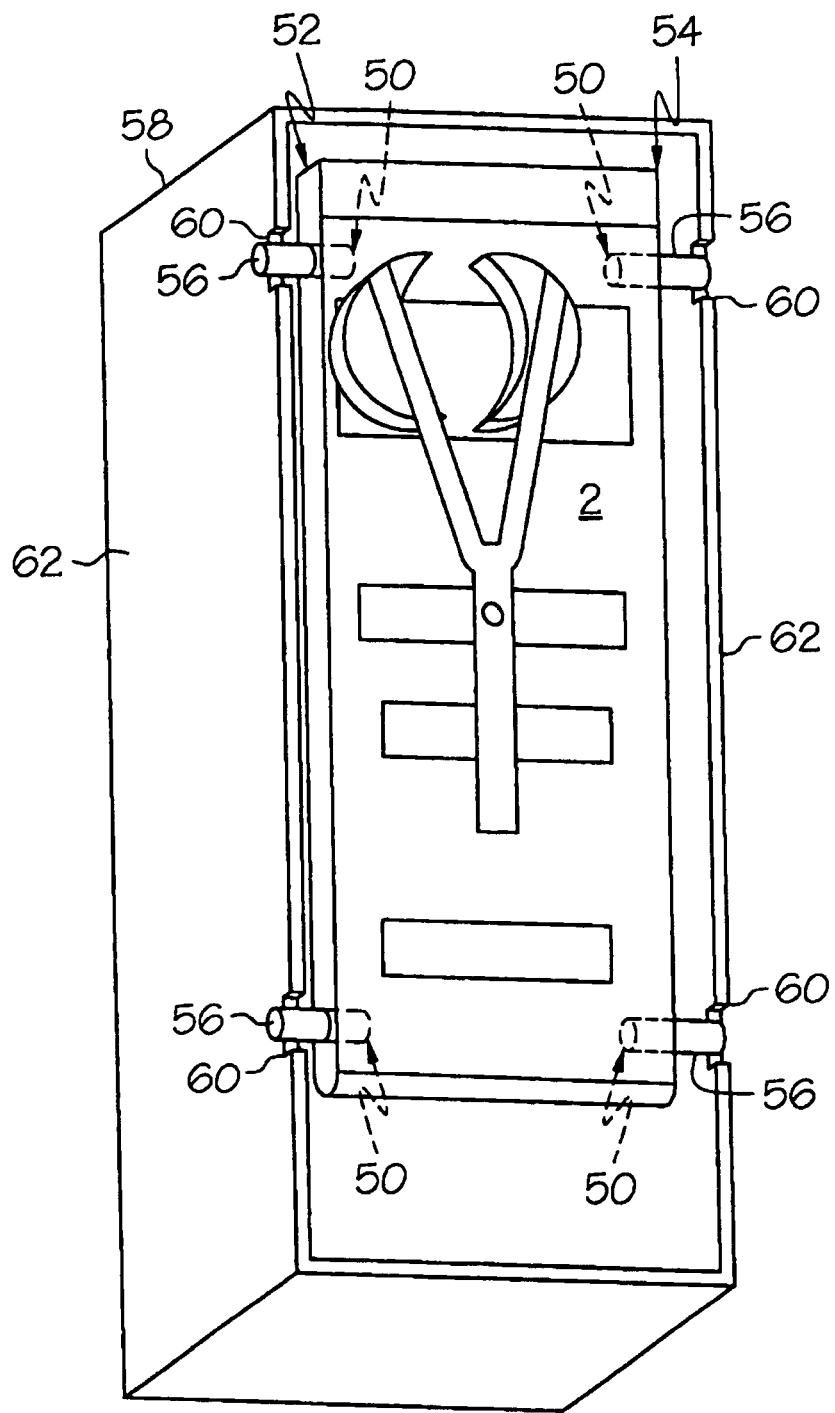

In another embodiment illustrated by FIG. 3b, the cover 4 and the infant backboard 43 may be provided with a pair of holes 50 in each long side 52 and 54, and sized to fit within the interior well diameter of a conventional isolette 58. These holes 50 may be used to accommodate ball-loc pins 56 that permit mounting of the infant backboard to the isolette 58. The advantage of such an embodiment is that an infant need not be removed from the immobilizer device 2 in order to be placed in the isolette 58, thereby minimizing the risk of further injury to the injured patient. Another advantage of such an embodiment is the safety appreciated by the board and cover locking into the isolette with the patient secured to the board and cover in the event of untoward motion during ground and/or air transport.

For the neonatal embodiment, spring load latches or slots 60 provided on sides 62 of the isolette 58 engage the ball-loc pins 56 to securely mount the infant backboard 43 thereon. In still another embodiment, the cover 4 and the isolette mattress (not shown) may include hook and loop fastening material to accomplish the same. It should be appreciated by those persons skilled in the related art, that other configurations and arrangements of securing elements may be provided in order to mount securely the cover 4 and the infant backboard 43 to the isolette 58.

Figure 4:
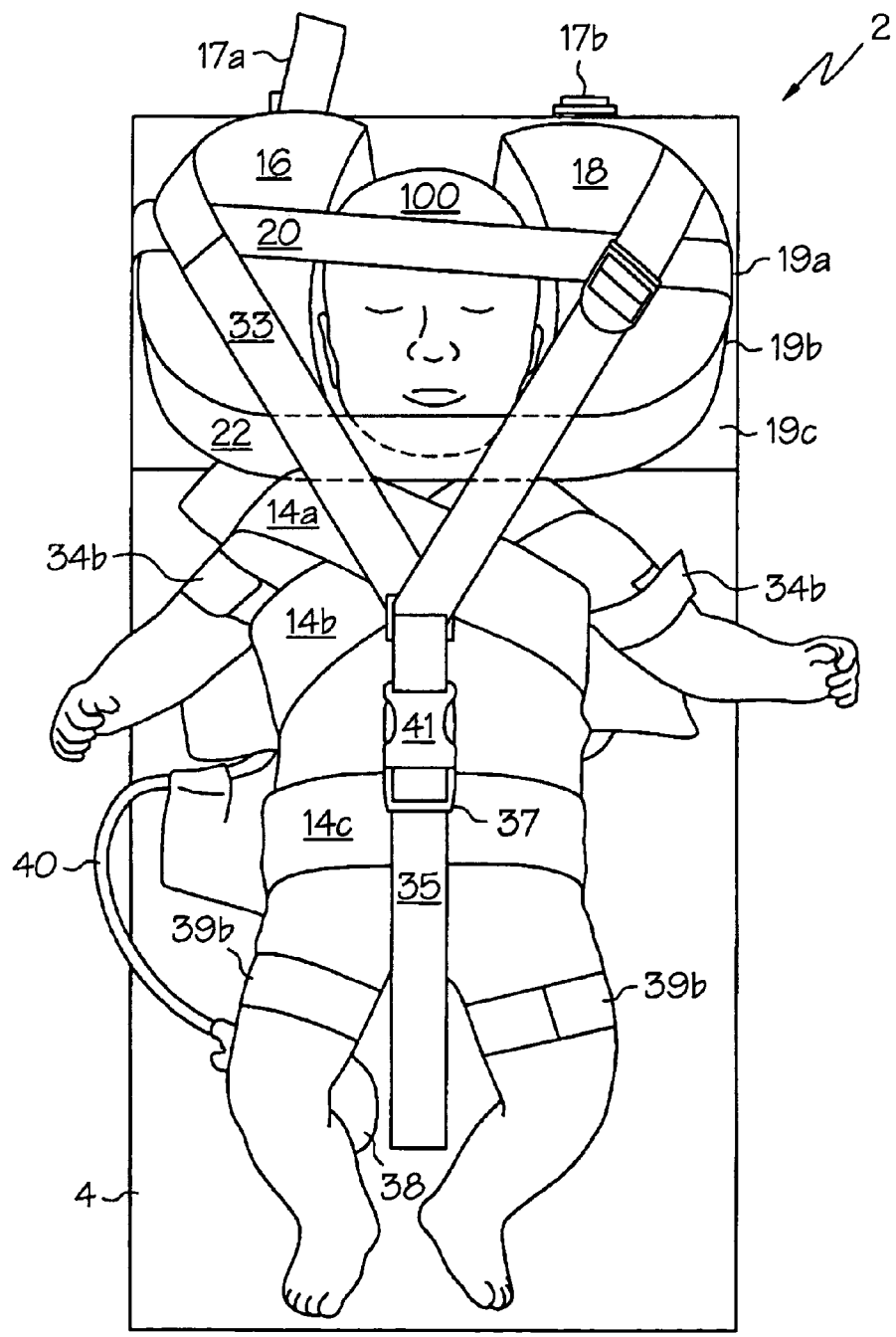
FIG. 4 is a front perspective view of the embodiment of FIG. 3a, showing an immobilized infant patient properly restrained in cervical radiographic-neutral alignment.

FIG. 4 is a front perspective view of an infant 100 properly restrained in the spinal immobilization device 2As shown, the body straps 14a and 14b are criss-crossed over the top of the infant's chest and body to provide for a firm fit such that the infant 100 may not wiggle or squirm out from under the body straps. With body strap 14c and leg restraints 39a and 39b placed firmly around the infant's waist and legs, respectively, the nipple-waist-knee restraining procedure is completed. Added control over the movement of the infant 100 is provided by holding firmly the infant's arms with the arm restraints 34a and 34b. As mentioned, the use of the arm restraints 34a and 34b permit the body straps 14a and 14b to be removed during examination, such as, for example, to administer intravenous therapy or to measure blood pressure, without risking further injury to the infant by restraining any side-to-side or twisting motions. However, for other embodiments, the arm and leg straps may not be provided. Additionally, with the headblocks 16 and 18 properly placed around the infant's head, the increased contact surface area from the headblocks' crescent shape and compressible foam material provide a slight separating force between the infant's head and shoulders, thereby minimizing undesirable lateral and flexion movement of the patient's head.

Figure 5:
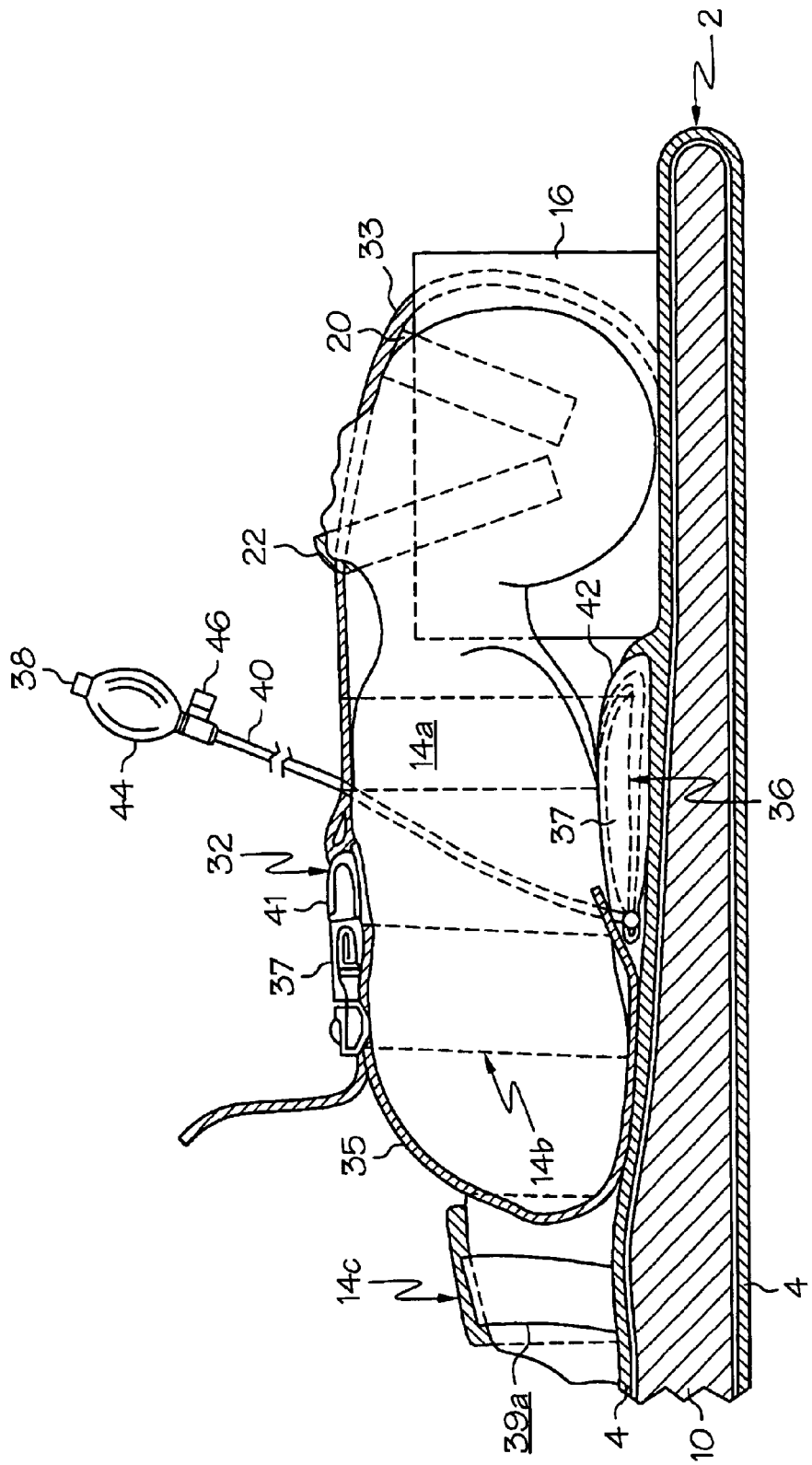
FIG. 5 is a side section view taken through an upper portion of the pediatric spinal immobilization device of the present invention showing an immobilized pediatric patient properly restrained in cervical radiographical-neutral alignment.

In the embodiments illustrated by FIGS. 1 and 3, the device 2 includes an elevation device, indicated by dashed line 36. The elevation device 36 and its use is best shown by FIG. 5, illustrating a side section view of the upper portion of the spinal immobilization device 2 immobilizing an injured pediatric patient in a proper cervical radiographic-neutral alignment, with the patient's back in the thorax region elevated to properly open an airway. In particular, the elevation device 36 permits a caregiver to raise or lower the thorax in small increments to align the external auditory meatus with the shoulders as the guideline to providing neutral cervical alignment and optimal airway opening. The elevation device 36 comprises an inflatable bladder 37 and an inflation device 38 in fluid communication with the inflatable bladder 37 through a tube 40. The inflatable bladder 37, such as the type provided by a blood pressure cuff, is contained within a compartment or pouch 42 preferably provided integrally with the fabric cover 4.

The inflatable bladder 37, when inflated as shown, allows a paramedic to space the thorax of the pediatric patient a sufficient distance from the backboard to prevent downward flexure of the patient's head toward the chest, and thereby maintain an open airway. Accordingly, this device is particularly useful in elevating the chest and upper back of a supine patient relative to the patient's head to open the patient's airway for CPR. It is to be appreciated that the system of headblocks 16 and 18, head straps 20, chin straps 22, body straps 14, harness 32, and inflatable bladder 36, functions to immobilize and correctly align the cervical spine of a pediatric patient. In particular, the harness 32 functions to retain the patient, proximate the thoracic spine, over inflatable bladder 37.

The inflation device 38 includes an air bulb 44 and an operator-controlled vent valve 46 to control inflation and deflation of the bladder 37. Accordingly, the range of about 0.5 cm to greater than 4 cm of elevation of a patient's back in the thorax region can be easily obtained and adjusted by inflating or deflating the bladder 37. With the addition of the headblocks providing a slight separating force between the head and shoulders, FIG. 5 demonstrates the effectiveness, safety, and novelty of the improved pediatric immobilizer. In FIG. 5, the patient'cervical spine is in the proper neutral position, and the patient is sufficiently immobilized with a fully open and unobstructed airway, thereby allowing for the safe and effective transportation of the patient to an appropriate medical facility.

In the foregoing specification, the invention has been described with reference to specific exemplary embodiments thereof. It should be appreciated that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A spinal immobilization device for a pediatric patient suffering from a trauma to the head, neck or back, comprising:
    a cover having on a front portion thereof a first securing element, a plurality of releasably attachable body straps each having a midsection mounted along a central section of said front portion to provide a degree of wrap around the pediatric patient, and at least a pair of releasably attachable arm and leg restraints;
    an elevation device on said front portion;
    a pair of headblocks each having, substantially convering on a side, a second securing element; and
    a harness having first, second, and third ends, said first end being mounted along said central section of said front portion such that said harness passes between the legs of the pediatric patient when accommodated in said device, and said second and third ends being mounted to said front portion such that said harness provides a degree of wrap to said headblocks and helps maintain the pediatric patient on said elevation device when accommodated in said device.

2. The spinal immobilization device of claim 1, further comprising a backboard securely fitted with said cover.

3. The spinal immobilization device of claim 1, wherein said cover further comprises a rear portion and a plurality of straps provided at on each end of said front and rear portions said ends of said front and rear portion being releasably fastened together with fastening elements provided on said plurality of straps.

4. The spinal immobilization device of claim 1, wherein said headblocks are made of a compressible material and are crescent-shaped and further include chin and head straps, each end of said chin and head straps being releasably mounted to said headblocks.

5. The spinal immobilization device of claim 1, wherein said elevation device comprises an inflatable bladder on said front portion, and an inflation device in fluid communication with said bladder for inflating and deflating said bladder.

6. The spinal immobilization device of claim 2, wherein said cover and said backboard include a plurality of holes accommodating pins configured to permit said device to be mounted to an isolette.

7. The spinal immobilization device of claim 3, wherein said cover further includes a plurality of side flaps for providing a degree of wrap.

8. The spinal immobilization device of claim 3, wherein said cover has cutout portions provided between said front and rear portions.

9. A restraint system for immobilizing on an adult-sized backboard having a plurality of hand slots, a pediatric patient suffering front a trauma to the head, neck and/or back, said restraint system comprising:
    a cover having a front portion, a rear portion and a cutout portion to expose at least a portion of said hand slots of the back board, said front portion providing a first securing element, a plurality of side flaps, and a plurality of adjustable straps releasably attaching ends of said front portion and said rear portion together, said plurality of side flaps being releasably attachable to said rear portion and providing a degree of wrap of said cover to the adult sized back board;
    a plurality of body straps each having a midsection mounted to a central section of said front portion of said cover to provide a degree of wrap around the body of the pediatric patient;
    a plurality of individual appendage restraints mounted to the front portion of said cover such that said body straps may be removed without losing control over the pediatric patient's appendages:
    an inflatable bladder provided on said cover to elevate the back in the thorax region of the pediatric patient;
    an inflatable device in fluid connection with said bladder for inflating and deflating said bladder;
    a pair of headblocks each providing, substantially on a side, a second securing element, such that said headblocks may be tightly yet removably attached to said first securing element; and
    a three point harness mounted to said front portion of said cover such that said harness helps to maintain the pediatric patient on said inflatable bladder and provides a degree of wrap to said pair of headblocks.

10. The restraint system of claim 9, wherein each of said headblocks is crescent-shaped and compressible.

11. The restraint system of claim 10, wherein said headblocks further include chin and head straps, each end of said chin and head straps being releasably mounted to said headblocks.

12. A spinal immobilization device for an infant patient under the age of about two months or about fifteen pounds suffering from trauma in the head, neck and/or back, said device comprising:
    a board appropriately sized for an infant;
    a cover providing a first securing element, said cover fitted over said board;
    an inflatable bladder provided on said cover for elevating the back in the thorax region of the infant patient;
    an inflation device in fluid connection with said bladder for inflating and deflating said bladder;
    a set of body straps each having a midsection mounted along a central section of said cover to provide a degree of wrap around the infant patient;

a pair of headblocks each providing, substantially on a side, a second securing element, such that said headblocks may be tightly yet removably attached to said first securing element; and a harness to deter undesirable head, shoulder, and neck movement, wherein said harness has a first end secured along said central section of said cover such that said harness may pass between legs of the infant patient when accommodated in said device, and second and third ends mounted adjacent said first securing surface such that said harness passes over each shoulder of the infant patient when accommodated in the device.

13. The spinal immobilization device of claim 12, wherein said pair of headblocks further includes releasably attachable chin and head straps.

14. The spinal immobilization device of claim 12 wherein said inflation device includes a compression bulb and vent valve.

15. The spinal immobilization device of claim 12 wherein said cover includes an integral pouch and said bladder is removably secured within said pouch.

16. The spinal immobilization device of claim 12, wherein free ends of said body straps each are connected via hook-and loop fastening material.

17. The spinal immobilization device of claim 12, wherein free ends of said straps are connected via hook-and loop fastening material.

18. The spinal immobilization device of claim 12, wherein each of said headblocks is crescent-shaped and made of a compressible material.

19. A method of supporting a pediatric patient on an adult-size backboard having a plurality of hand slots, said method comprising:

fitting a cover providing a plurality of centrally mounted body straps, a plurality of individual appendage restraints, a three point harness, and a first mating surface;

securing the pediatric patient to said cover using said plurality of centrally mounted body straps to provide a degree of wrap around at least the chest, waist, and knees of the pediatric patient, and a said plurality of individual appendage restraints such that said body straps may be removed without losing control over the pediatric patient's appendages;

providing a pair of compressible, crescent-shaped headblocks, each of said headblocks having on a rear side a second mating surface such that each of said headblocks is tightly yet removably attached to said first mating surface;

inflating an inflatable bladder provided onto said cover to open an airway by elevating the pediatric patient's back in the thorax region; and adjusting said three-point harness provided to said cover to position the pediatric patient on said inflatable bladder and to deter undesirable head, shoulder, and neck movement.

20. The method of claim 19, further comprising securing the pediatric patient's head with a chin strap and a head strap that are releasably secured at their respective ends to said headblocks.

* * * * *

UNITED STATES PATENT AND TRADEMARK OFFICE
CERTIFICATE OF CORRECTION

PATENT NO. : 6,966,087 B2
APPLICATION NO. : 10/489294
DATED : November 22, 2005
INVENTOR(S) : Lydia Marie Robinette It is certified that error appears in the above-identified patent and that said Letters Patent is hereby corrected as shown below:

Col. 9, Line 42, "convering" should read --covering--
Col. 9, Line 57, "portions" should read --portions,--
Col. 10, Line 15, "front" should read --from--
Col. 10, Line 34, "appendages:" should read --appendages;--
Col. 12, Line 9, "and a said" should read --and said--
Col. 12, Line 19, "provided onto" should read --provided to--
Col. 12, Line 23, "harness provided to said cover to" should read --harness to--

Signed and Sealed this

First Day of August, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,966,087 B2 | Page 1 of 1 |
| APPLICATION NO. | : 10/489294 | |
| DATED | : November 22, 2005 | |
| INVENTOR(S) | : Lydia Marie Robinette | |

It is certified that error appears in the above-identified patent and that said Letters Patent is hereby corrected as shown below:

Col. 10, Line 37, "inflatable" should read --inflation--.

Signed and Sealed this

Twenty-first Day of November, 2006

JON W. DUDAS
*Director of the United States Patent and Trademark Office*